United States Patent
Law et al.

(10) Patent No.: US 7,207,220 B2
(45) Date of Patent: Apr. 24, 2007

(54) FLUID COUPLING FOR A CHROMATOGRAPH

(75) Inventors: Clayton E. Law, Malvern, PA (US); Richard P. White, Glen Mills, PA (US); Sammye E. Miller, New Castle, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 195 days.

(21) Appl. No.: 11/058,125

(22) Filed: Feb. 15, 2005

(65) Prior Publication Data

US 2006/0179920 A1 Aug. 17, 2006

(51) Int. Cl.
*G01F 15/14* (2006.01)
(52) U.S. Cl. .................................................. 73/432.1
(58) Field of Classification Search ................. 73/432.1
See application file for complete search history.

(56) References Cited

U.S. PATENT DOCUMENTS

| | | | | |
|---|---|---|---|---|
| 1,989,955 A | * | 2/1935 | Patter ........................ 403/281 |
| 2,926,937 A | * | 3/1960 | Parsons ....................... 285/350 |
| 3,403,717 A | * | 10/1968 | Lemelson .................... 411/143 |
| 5,433,454 A | * | 7/1995 | Ramberg ..................... 277/643 |
| 5,567,868 A | * | 10/1996 | Craig et al. ................ 73/23.42 |
| 5,640,751 A | * | 6/1997 | Faria ........................ 29/525.02 |
| 5,767,384 A | * | 6/1998 | Wang et al. ............... 73/23.21 |
| 5,767,387 A | * | 6/1998 | Wang ........................ 73/23.42 |
| 5,803,507 A | * | 9/1998 | Vu ............................... 285/23 |
| 5,804,701 A | * | 9/1998 | Berger ....................... 73/23.42 |
| 5,868,109 A | * | 2/1999 | Kunzel et al. ........... 123/90.38 |
| 6,450,506 B1 | * | 9/2002 | Krieg et al. ................ 277/608 |
| 6,612,153 B2 | | 9/2003 | White et al. |
| 6,701,774 B2 | * | 3/2004 | Srinivasan et al. ........ 73/23.42 |
| 6,862,916 B2 | * | 3/2005 | Cordill ...................... 73/23.42 |

* cited by examiner

*Primary Examiner*—Hezron Williams
*Assistant Examiner*—John Fitzgerald (57) ABSTRACT

A fluid coupling comprises a compliant material, a seal gland having at least one projection configured to contact the compliant material, and a cover plate configured to compress the compliant material into the gland, thus forcing the compliant material against the projection.

8 Claims, 6 Drawing Sheets

FLUID COUPLING FOR A CHROMATOGRAPH

BACKGROUND

Many chemical analysis applications use one or more sample tubes to collect, concentrate, and transfer a representative sample of a material to an analysis device. For example, gas chromatography involves vaporizing a sample and injecting the vaporized sample onto the head of a chromatographic column. The column is one of several fluidic components in the instrument. The sample is transported through this column by the flow of an inert gaseous mobile phase, also referred to as a carrier gas. The chromatographic column contains a liquid stationary phase that is absorbed onto the surface of an inert solid. The organic compounds in the sample are separated due to differences in their partitioning behavior between the mobile gas phase and the stationary phase in the column. Since the partitioning behavior is dependant on temperature, the separation column is usually contained in a thermostat-controlled oven. Separating components with a wide range of boiling points is accomplished by starting at a low oven temperature and increasing the temperature over time to elute the high-boiling point components. A detector is used to determine what compounds elute from the sample and a recorder provides the output in the form of a chromatograph.

Each of the fluidic components that comprise the instrument's fluid flow paths needs to be inter-connected to create an overall fluid flow network. Furthermore, many of these fluid connections need to be repeatedly disconnected and reconnected for several reasons, including maintenance of the instrument and system reconfiguration. Therefore, a reusable, leak-tight fluid connection or coupling is desirable.

There are a variety of fluidic sealing devices that can provide this type of fluidic connection. Among these devices are metal fittings and ferrules, gaskets and o-rings. Specific geometry and applications where o-ring seals are used can further characterize an o-ring fluidic connection as static, dynamic, radial, face and combinations of these. One of the most common, because it is simple and economical, is a static face-seal o-ring. In addition to low material and assembly cost, static face-seal o-ring connections provide several advantages over other common fluid sealing devices, such as being compact, simple, reusable and durable. When properly applied, static face-seal o-ring connections typically leak no more than $1.8 \times 10^{-5}$ std. cc/sec Helium at 300 psig.

Unfortunately, o-rings in face-seal applications suffer from several limitations. They will leak if either sealing surface is rough, scratched or contaminated with particles or fibers. Surface finishes of 32 microinches RMS with no scratches, gouges or other imperfections are typically required to ensure a fluid-tight seal. In addition, o-rings are subject to physical damage during their manufacture, storage, handling, shipping and assembly into their sealing detail which may ultimately result in seal failure. Finally, particulate and fiber contamination easily adhere to the o-ring surfaces, which can affect seal performance. Special cleanliness requirements exist to achieve typical desired seal performance. These limitations result in less than 100% yield, especially in a fluidic network containing multiple fluid connections, such as in the assembly of a gas chromatograph instrument. The cost of troubleshooting and repair motivates the search for an improved fluidic coupling.

SUMMARY OF INVENTION

According to one embodiment, a fluid coupling comprises a compliant material, a seal gland having at least one projection configured to contact the compliant material, and a cover plate configured to compress the compliant material into the gland, thus forcing the compliant material against the projection.

Other embodiments and methods will be discussed with reference to the figures and to the detailed description of the preferred embodiments.

BRIEF DESCRIPTION OF THE FIGURES

The invention will be described by way of example, in the description of exemplary embodiments, with particular reference to the accompanying figures.

DETAILED DESCRIPTION

While described below for use in a gas or liquid chromatograph, the fluid coupling to be described below can be used in any analysis application where it is desirable to couple two or more elements to form a fluid-tight seal. For example, the fluid coupling can also be used in an auxiliary flow module. The fluid coupling improves the design robustness of static o-ring face-seals by reducing their sensitivity to sealing surface imperfections and contamination introduced to the sealing surfaces by introducing a projection that contacts the compliant material that forms the seal.

The fluidic coupling includes a projection seal design that has four primary advantages over the traditional face-seal o-ring. First, the projection's relatively small surface area is the cause for the relatively high local sealing stress at the sealing boundary. This sealing stress forms the compliant sealing member's shape to the projection's crest, providing the seal. By maximizing the sealing stress at the sealing boundary, the sealing function is maximized while minimizing possible overstress of the compliant material. Second, the relatively smaller projection sealing area provides reduced opportunity for surface imperfections compared with the relatively larger sealing gland area of a traditional seal. Third, the higher sealing stress provides increased sealing robustness against particulate and fiber contamination on the sealing surfaces. Fourth, assembling the compliant material onto the projection sealing area generates a wiping action across the projection sealing area. This wiping action tends to remove particulate and fiber contamination to the well or wells created by the projection. The wells capture this debris during assembly of the fluid coupling.

Figure 1:
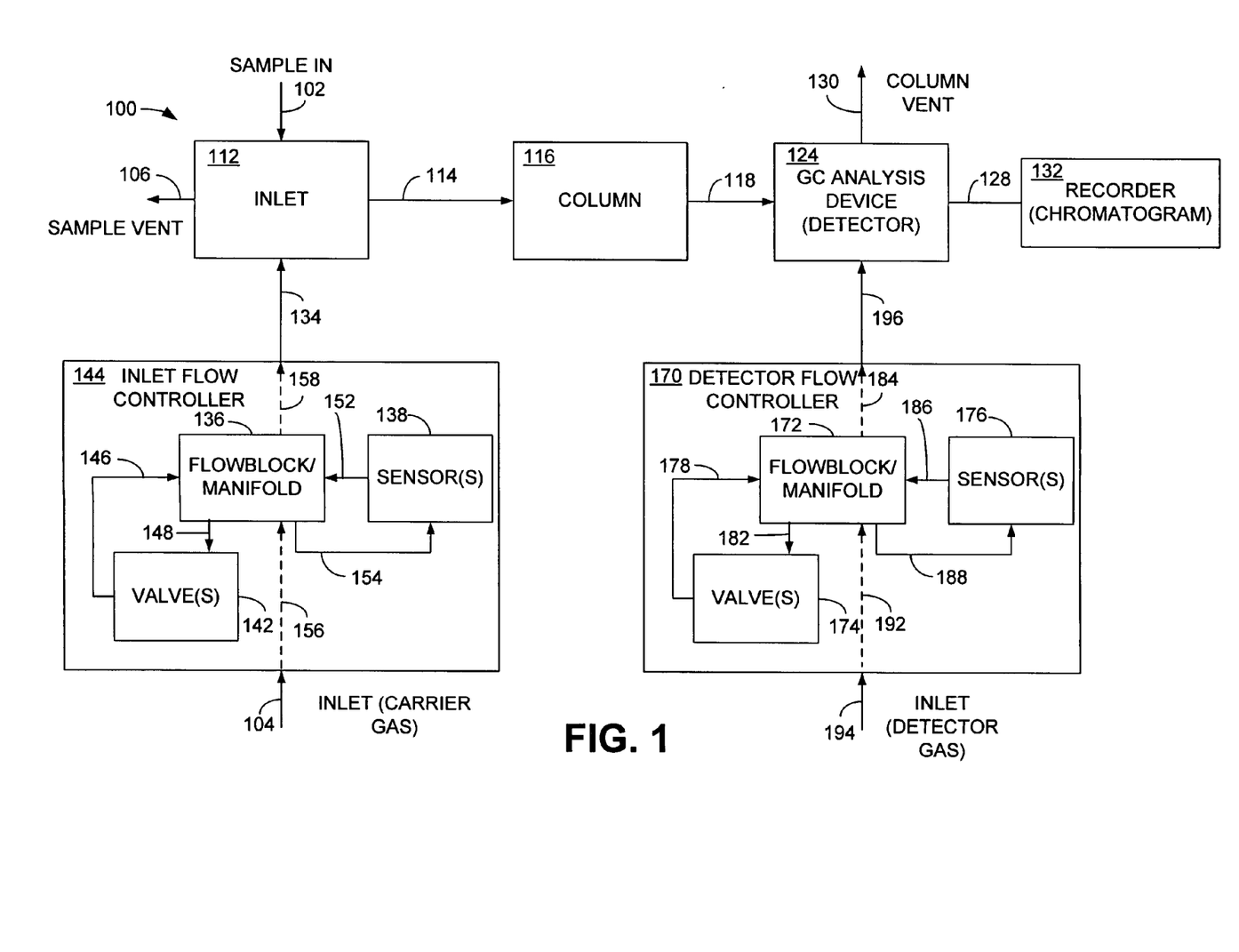
FIG. 1 is a schematic diagram illustrating a simplified chromatograph in which a fluid coupling constructed in accordance with an embodiment of the invention may reside.

FIG. 1 is a block diagram illustrating a simplified gas chromatograph 100, which is one possible device in which the fluid coupling of the invention may be implemented. The fluid coupling may also be used in any gas phase sampling device or in any analytical device, and may also be useful for liquid phase couplings. The fluid coupling can be used to couple pneumatic elements, such as valves and pressure sensors, to a pneumatic manifold such as a pneumatic flow block, or to various other types of fluid containing devices.

The gas chromatograph 100 includes an inlet 112 where a sample to be analyzed is introduced into the instrument via a sample port 102. The gas chromatograph 100 also includes an analytical column 116 where the chemical separation is performed, and a detector 124 where the chemical components of the sample are detected. An inlet 112 typically has two supply flows. The clean inert carrier gas is supplied via connection 104 through an inlet flow controller 144 and the chemical sample to be analyzed is usually introduced to the sample port 102 via a syringe and subsequently vaporized. The inlet 112 may include a vent port 106 to vent excess sample material.

The detector 124 is similarly supplied one or more gases via port 194 in the detector flow controller 170. Once the sample has been detected it is vented from the detector 124 through the column vent 130.

Each of the flow controllers 144 and 170 comprise several fluidic components that operate together to provide metered flow. The inlet flow controller 144 comprises a fluid manifold or flow block 136 to aid in both mechanical and pneumatic connection of the fluidic components. Depending on the application (inlet, detector, etc.) a flow controller may include one or more sensors 138 to provide measurement and feedback of the flow to be metered and one or more valves 142 to perform the metering. Other elements have been omitted to simplify FIG. 1. For example, the flow controllers also include one or more fluidic restrictive devices to further control fluid flow.

Similarly, the detector flow controller 170 comprises a fluid manifold or flow block 172 to aid in both mechanical and pneumatic connection of the fluidic components. The flow controller 170 also comprises one or more sensors 176 to provide measurement and feedback of the flow to be metered and one or more valves 174 to perform the metering.

The gas chromatograph 100 includes a number of fluid couplings. The fluid couplings 114 and 118 that couple the column 116 to the inlet 112 and the detector 124, respectively, are able to operate under elevated temperatures and are chemically inert.

The gas chromatograph 100 also includes fluid couplings 134 between the inlet flow controller 144 and the inlet 112, and the fluid coupling 196 between the detector flow controller 170 and the detector 124, as well as the fluid connections 146, 148, 152, 154, 156 and 158 in the inlet flow controller 144, and fluid couplings 178, 182, 184, 186, 188 and 192 in the detector flow controller 170. The fluid couplings 134, 196 and the fluid couplings in the inlet flow controller 144 and in the detector flow controller 170 are designed to be repeatedly disconnected and reconnected and use an o-ring or other compliant material to form the seal in accordance with embodiments of the invention.

Figure 2:
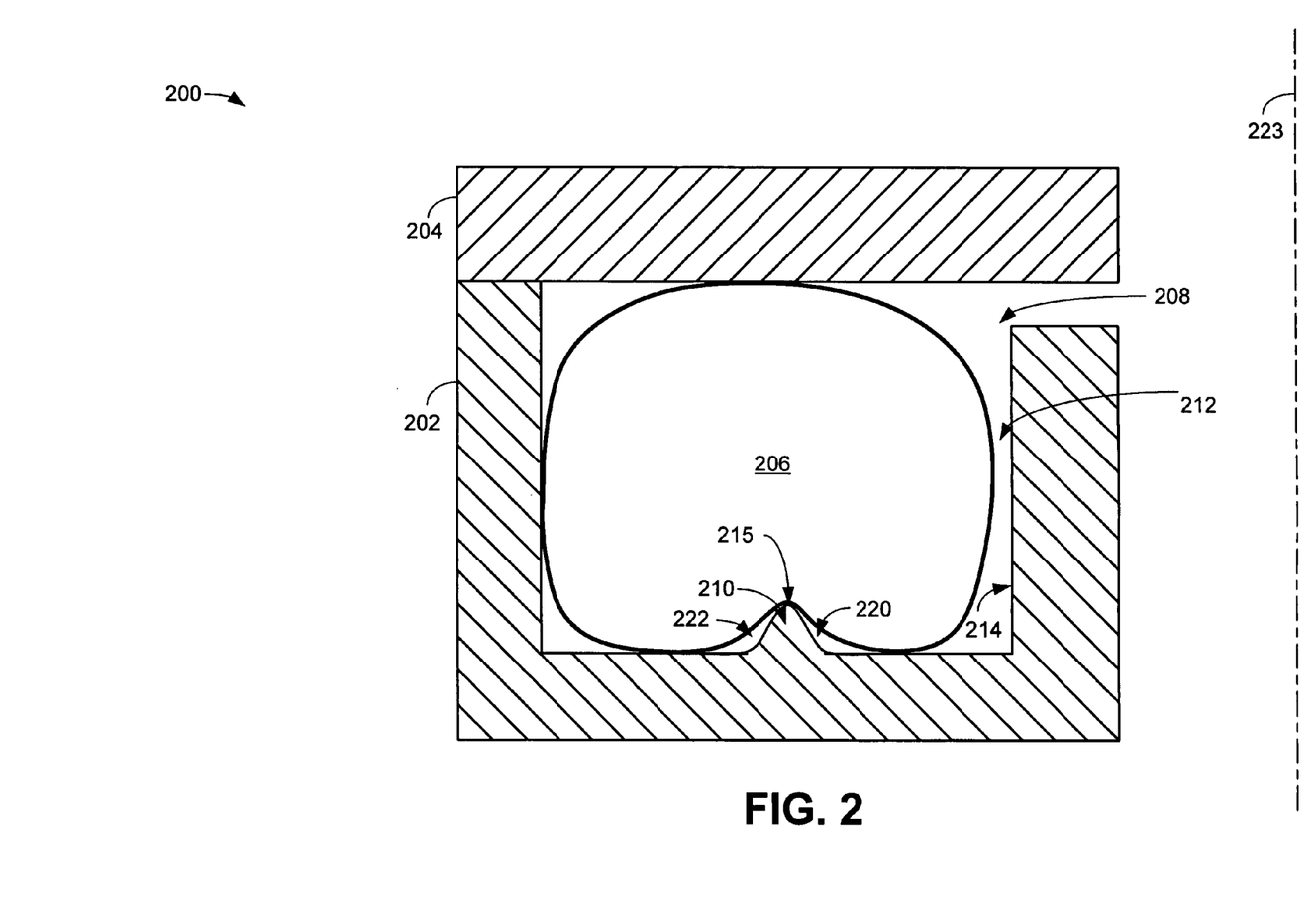
FIG. 2 is a schematic diagram illustrating a cross-sectional view of a first embodiment of the fluid coupling of FIG. 1.

FIG. 2 is a schematic diagram illustrating a cross-sectional view of a first embodiment of the fluid coupling 134 of FIG. 1. The fluid coupling 134 is used for example only. Other fluid couplings in FIG. 1 may be similarly fabricated.

The fluid coupling 134 comprises a base portion 202 defining a seal gland 208, sometimes referred to as a gland. For example, the base portion 202 can be part of the flow block 136 of FIG. 1. The centerline 223 represents the centerline around which the fluid seal is located. The base portion 202 includes a projection 210. The projection 210 can be formed as part of the base portion 202 or can be a separate element added to the base portion 202. Further, the projection 210 can have other shapes than what is shown in FIG. 2. The projection 210 can be formed as an annular or concentric feature within the gland 208 or may be one or more discrete projections that can be annular, concentric rings, a singular interrupted concentric ring, or any other projection. The projection 210 may be formed by, for example, machining, etching, casting or other techniques. The projection can be of various profiles and, as shown in this embodiment, includes a rounded tip, referred to as a crest 215.

A compliant material 206 occupies the gland 208. A cover plate 204 covers the compliant material 206, and when pressure is applied to secure the cover plate 204 to the base portion 202, compresses the compliant material 206 in the gland 208 and against the projection 210, thus forming a fluid tight seal along the projection 210. Although omitted from FIG. 2 for clarity, the cover plate 204 may be secured to the base portion 202 by screws, adhesive, or other known fastening techniques. The crest 215 presses against the compliant material 206 forming wells 220 and 222 approximately as shown. The wells 220 and 222 can trap particulate and fiber contamination that may be present on the compliant material 206 or in the gland 208. In another embodiment, the compliant material 206 can be fabricated with a groove or recess designed to receive the projection 210. The compliant material 206 can be, for example, a toroidal-shaped o-ring gasket, a rectangular gasket, a metallic gasket, or another type of compliant material. In one embodiment, the gland 208 is dimensioned to accept an o-ring having an outer diameter of 0.254 inches (in.), an inner diameter of 0.114 in. and a cross-sectional diameter of 0.070 in. The compliant material 206 can be fabricated of a fluoroelastomer material known as Viton®, a registered trademark of DuPont Dow Elastomers. A gap 212 is likely to be created between the compliant material 206 and the wall 214 of the gland 208. This is due to the higher pressure on one side of the o-ring and the lower ambient pressure on the opposite surface of the o-ring.

A fluoroelastomer is a high performance synthetic rubber with excellent resistance to chemicals and oils at elevated temperatures. This material is desired because it can effectively operate in a temperature range from −40° F. (−40° C.) to 500° F. (260° C.). Furthermore, this temperature range can be exceeded for short periods of time. The temperature performance, together with superior chemical resistance, make fluoroelastomer a good choice for fluid seals in chromatographic applications.

Perfluoroelastomers, including Kalrez® (a registered trademark of DuPont Dow Elastomers) and Chemraz® (a registered trademark of Green, Tweed Corp.), are also suitable chemical and temperature resistant sealing materials for gas and liquid chromatographic sealing applications. Further, other elastomers, such as nitrile materials, also may be used in these applications.

Thin film coatings can be applied to the projection 210. Physical Vapor Deposition (PVD) and Chemical Vapor Deposition (CVD) are two common types of thin-film coating methods. Possible materials for coating the projection 210 include, but are not limited to, titanium carbonate, titanium aluminum nitride, titanium nitride, chromium nitride, zirconium nitride and amorphous diamond-like carbon (DLC).

In accordance with an embodiment of the fluid coupling 134, the projection 210 presses into the compliant material 206 as a result of the cover plate 204 being secured to the base portion 202 and the compliant material 206 being compressed into the gland 208. The projection 210 deforms the compliant material 206 such that a fluid-tight coupling is created.

Figure 3:
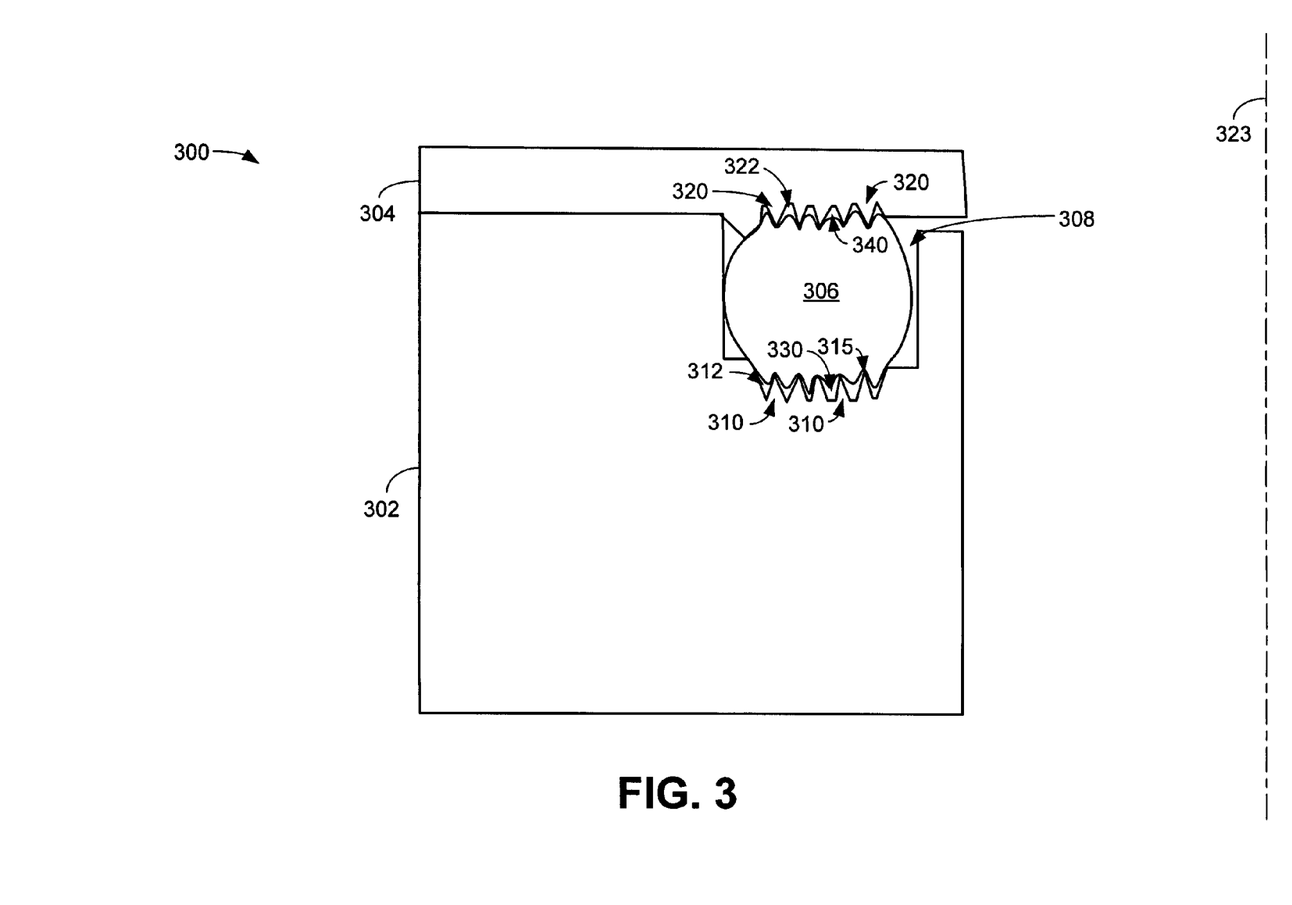
FIG. 3 is a schematic diagram illustrating a cross-sectional view of an alternative embodiment of the fluid coupling of FIG. 2.

FIG. 3 is a schematic diagram illustrating a cross-sectional view of an alternative embodiment 300 of the fluid coupling of FIG. 2. The fluid coupling 300 comprises a base portion 302 that defines a gland 308. The centerline 323 represents the centerline around which the fluid seal is located. The base portion 302 includes, in this embodiment, a plurality of projections 310, defining a plurality of recesses 312. The projections 310 and the recesses 312 can be formed in the base portion by, for example, machining, etching, casting or other techniques. The projections 310 can be periodic or non-periodic in spacing, and can be of differing heights and profiles, depending on application. The crests 315 of the multiple projections provide redundant sealing. Each recess 312 defines a well 330. The well 330 is designed to capture particulate matter, fibers and other debris that may become trapped in the gland 308 during assembly of the fluid coupling 300. Assembling the compliant material onto the projection sealing areas generates a wiping action across the crests. This wiping action will tend to remove particulate and fiber contamination into the wells 330 that act to capture such debris during assembly of the fluid coupling 300. When captured in a well 330, such debris is held away from the fluid sealing portions of the fluid coupling 300 and will not hinder the operation of the fluid coupling 300.

The fluid coupling 300 also includes a cover plate 304 having a plurality of projections 320 and recesses 322. Similar to the projections 310 and recesses 312, the projections 320 and recesses 322 can be periodic or non-periodic in spacing and can have differing heights and profiles, depending on application. Each recess 322 forms a well 340 that is similar in structure and function to the wells 330 in the base portion 302.

During assembly, the compliant material 306, which in this example is an o-ring type gasket, is placed in the gland 308 and the cover plate 304 is located over the compliant material 306 and secured to the base portion 302. Although omitted from FIG. 3 for clarity, the cover plate 304 may be secured to the base portion 302 by screws, adhesive, or other known fastening techniques. The compliant material 306 and the gland 308 are dimensioned such that, when the cover plate 304 is firmly attached to the base portion 302, the compliant material 306 is pressed into the gland 308 and distorts so that a portion of the compliant material 306 at least partially fills the recesses 312 in the base portion 302 and the recesses 322 in the cover plate 304. In this manner, additional fluid sealing integrity is provided because the material from which the compliant material 306 is fabricated is flexible and at least partially fills the recesses 312 and 322.

In addition, particulate or fibrous contaminant matter that may span multiple projections 310, will likely be forced into one or more wells 330, thus reducing the possibility that such contamination will cause the fluid coupling 300 to leak and the seal to fail. In an alternative embodiment, the cover plate 304 need not include the projections 320 and the recesses 322 and the fluid coupling 300 would rely on the projections 310 and the recesses 312 to achieve a fluid seal. In such an embodiment, a conventional o-ring seal is created where the compliant material 306 meets the surface of the cover plate 304.

Figure 4A:
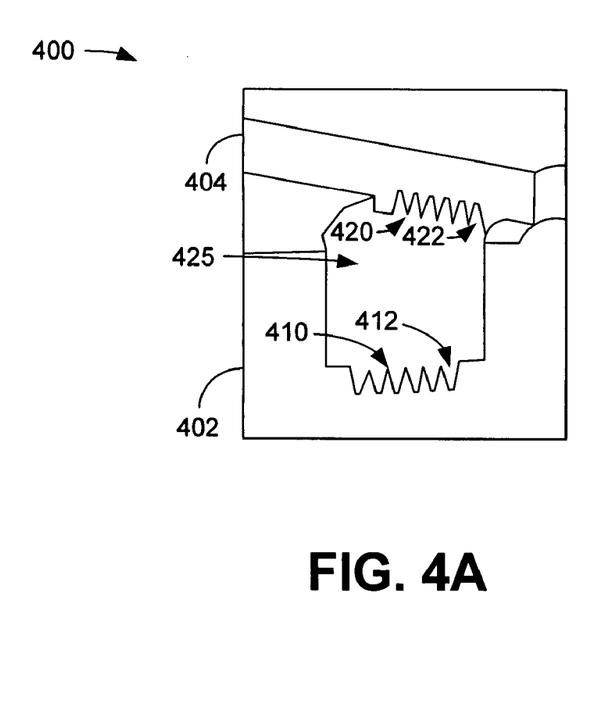
FIGS. 4A and 4B are schematic diagrams collectively illustrating the fluid coupling of FIG. 3 in perspective view.
Figure 4B:
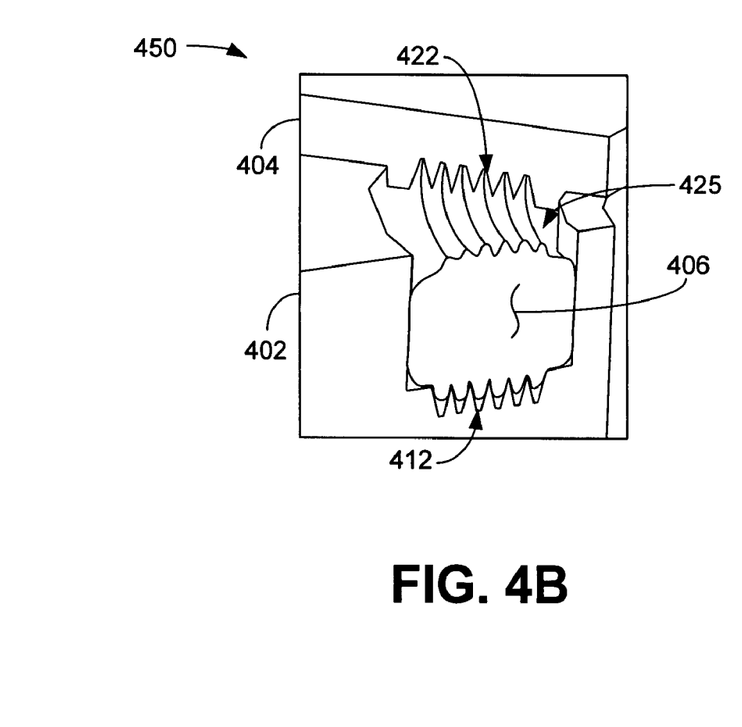

FIGS. 4A and 4B are schematic diagrams collectively illustrating the fluid coupling 300 of FIG. 3 in perspective view. In FIG. 4A, a base portion 402 defines a gland 425 into which a compliant material (omitted for clarity) can be inserted. The base portion 402 also includes a plurality of projections 410 and recesses 412. A cover plate 404 includes a similar plurality of projections 420 and recesses 422, but may also be a smooth planar surface.

In FIG. 4B, a compliant material 406 is located in the gland 425. The cover plate 404 is firmly attached to the base portion 402, thus compressing the compliant material 406 so that portions of the compliant material 406 deform and at least partially fill the recesses 412 and 422 in the base portion 402 and cover plate 404, respectively. In this manner, a fluid-tight seal is created that is resistant to leaking due to the presence of contamination or particulate matter on the compliant material 406 during assembly. In an alternative embodiment, the compliant material 406 can be formed to include ridges corresponding to the recesses 412 and 422, thus making it easier for portions of the compliant material 406 to at least partially fill the recesses 412 and 422. It should be mentioned that the base portion 402 can be implemented with a cover plate 404 having a substantially planar surface in contact with the compliant material 406 and in which only the projections 410 and recesses 412 would be present.

Figure 5A:
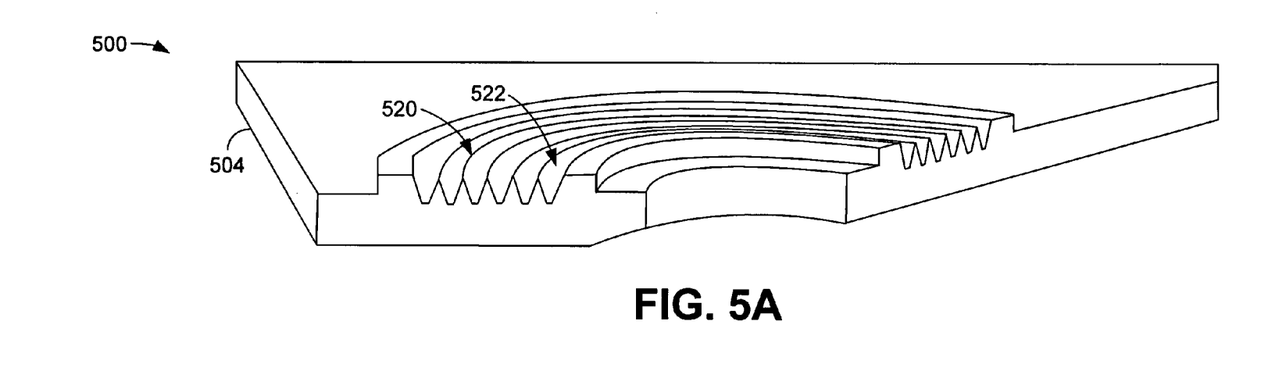
FIGS. 5A and 5B are schematic diagrams collectively illustrating a perspective view of a portion of the cover plate and the base portion of the fluid coupling of FIGS. 4A and 4B.
Figure 5B:
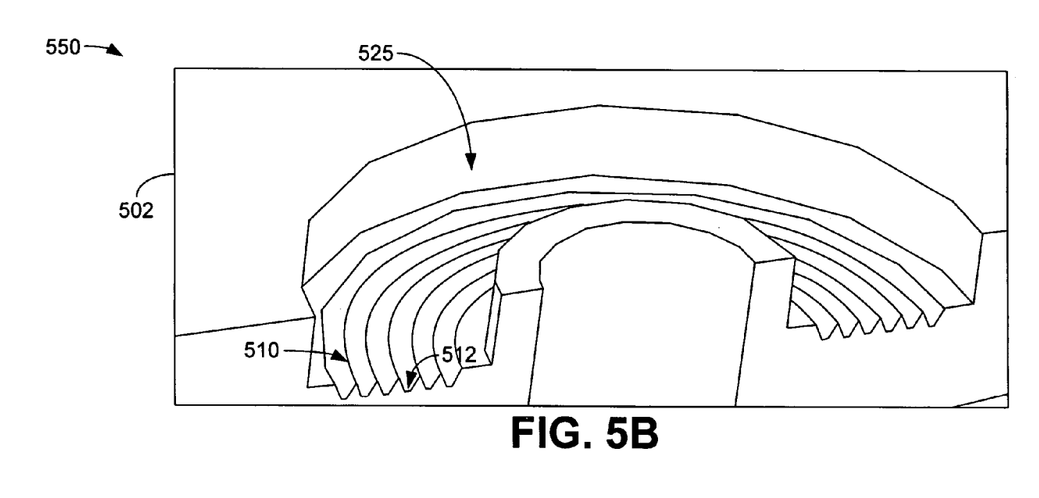

FIGS. 5A and 5B are schematic diagrams collectively illustrating a perspective view of a portion of the cover plate and the base portion of the fluid coupling of FIGS. 4A and 4B. In FIG. 5A, the cover plate 504 includes a plurality of projections 520 defining recesses 522. Although shown as being periodic in spacing and of equal height, the projections 520 and corresponding recesses 522 can be non-periodic in spacing and can be of differing heights and profiles.

FIG. 5B shows a cutaway view of a base portion 502 defining a gland 525. The gland 525 is the area in which a compliant material, such as an o-ring, will be placed. The base of the gland 525 includes projections 510 defining recesses 512. Similar to that described above, the projections 510 and corresponding recesses 512 can be period or non-periodic in spacing and can be of differing heights. As shown in FIGS. 5A and 5B, the projections 520 and corresponding recesses 522 are concentric in nature, and when produced would be a continuous annular feature of the base portion 502 and, if implemented, the cover plate 504. It should be mentioned that the base portion 502 can be implemented with a cover plate 504 having a substantially planar surface in contact with the compliant material and in which only the projections 510 and recesses 512 would be present.

Furthermore, the projections and recesses shown in FIGS. 2, 3, 4A, 4B, 5A and 5B can be coated with an additional material or combination of additional materials to provide additional properties and functions. For example, one or more treatments or coatings can be applied to the projections and recesses to alter texture, porosity, or other definable features to improve the seal. For example, the surfaces of the projections and recesses can be coated with a thin layer of a PTFE-like material to minimize friction between the compliant material and the gland surfaces. Alternatively, silver plating would provide a soft, compliant surface on the projections to reduce or eliminate potential leak sources due to surface imperfections. Electroless nickel would fill in surface imperfections and provide a smooth sealing surface.

Figure 6:
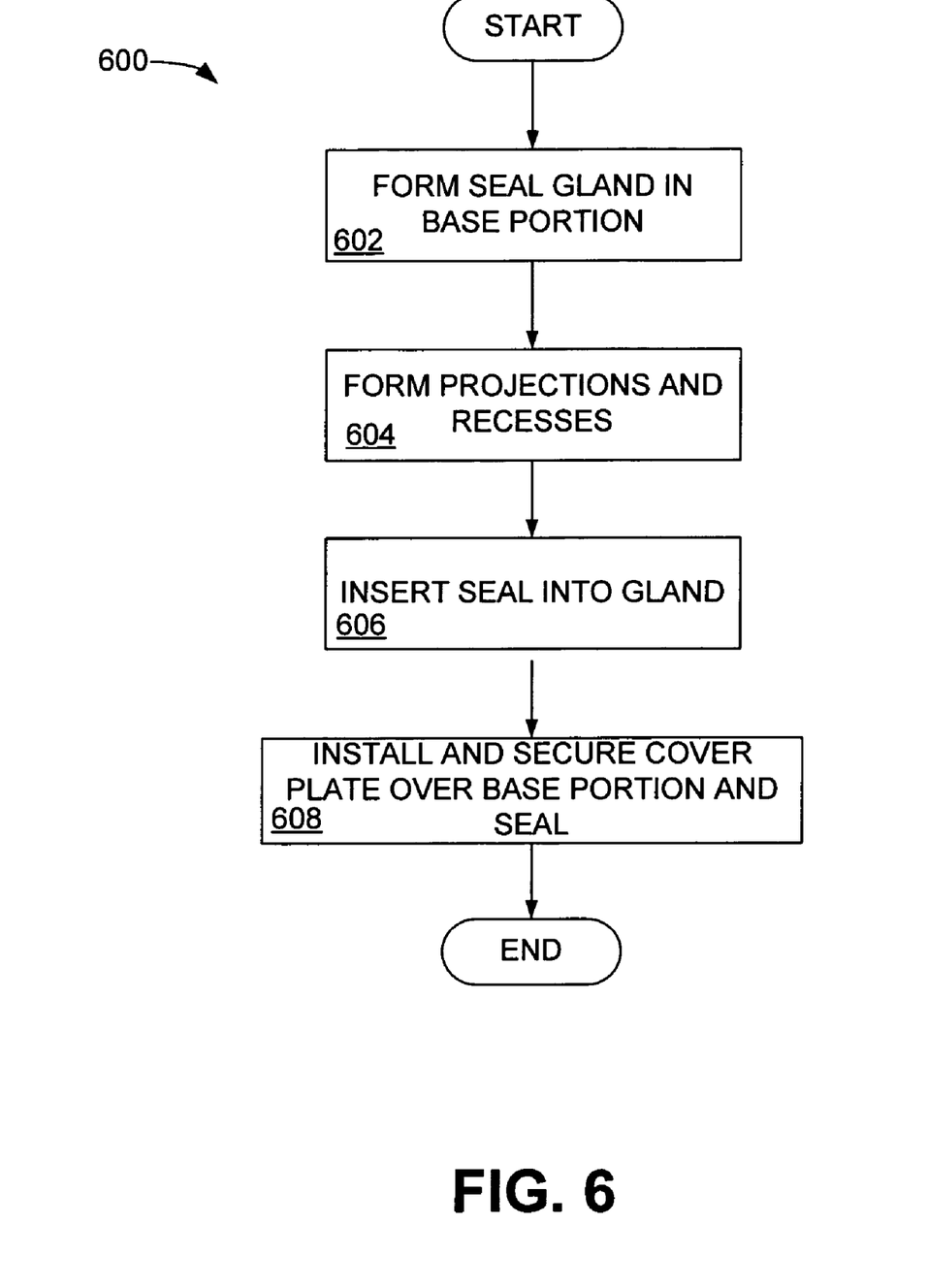
FIG. 6 is a flow chart describing a method for forming a fluid coupling.

FIG. 6 is a flow chart 600 describing a method for forming a fluid coupling. In block 602, a gland is formed in a base portion of a flow block. In block 604, projections and corresponding recesses are formed in the base portion. In block 606, a compliant material is inserted into the gland. In block 608, a cover plate is installed and securely fastened to the base portion, thus creating a fluid-tight seal.

The foregoing detailed description has been given for understanding exemplary implementations of the invention and no unnecessary limitations should be understood therefrom as modifications will be obvious to those skilled in the art without departing from the scope of the appended claims and their equivalents. Other devices may use the fluid coupling described herein.

We claim:

1. A fluid coupling for a gas chromatograph, comprising:
   a chromatographic column;
   an inlet and a detector in fluid communication with the chromatographic column;
   a flow block in fluid communication with the inlet and the detector;
   a seal surface on the flow block;
   a seal gland having at least one projection configured to contact a compliant material; and
   a cover plate configured to compress the compliant material into the gland, thus forcing the compliant material against the projection.

2. The fluid coupling of claim 1, wherein the seal gland and the cover plate further comprise a plurality of projections configured to compress the compliant material into the gland.

3. The fluid coupling of claim 2, wherein the projections in the seal gland define a plurality of recesses configured to at least partially receive portions of the compliant material and to capture debt.

4. The fluid coupling of claim 3, wherein a distance between the projections is periodic.

5. The fluid coupling of claim 3, wherein a distance between the projections is non-periodic.

6. The fluid coupling of claim 3, further comprising a coating on the projections and recesses.

7. The fluid coupling of claim 3, wherein the compliant material is an o-ring.

8. The fluid coupling of claim 3, wherein the compliant material includes at least one recess configured to receive at least one of the projections.

* * * * *

UNITED STATES PATENT AND TRADEMARK OFFICE
CERTIFICATE OF CORRECTION

PATENT NO. : 7,207,220 B2 Page 1 of 1
APPLICATION NO. : 11/058125
DATED : April 24, 2007
INVENTOR(S) : Law et al.

It is certified that error appears in the above-identified patent and that said Letters Patent is hereby corrected as shown below:

In column 8, line 11, in Claim 3, delete "debt" and insert -- debris --, therefor.

Signed and Sealed this

Thirty-first Day of July, 2007

JON W. DUDAS
*Director of the United States Patent and Trademark Office*